Figure 1:
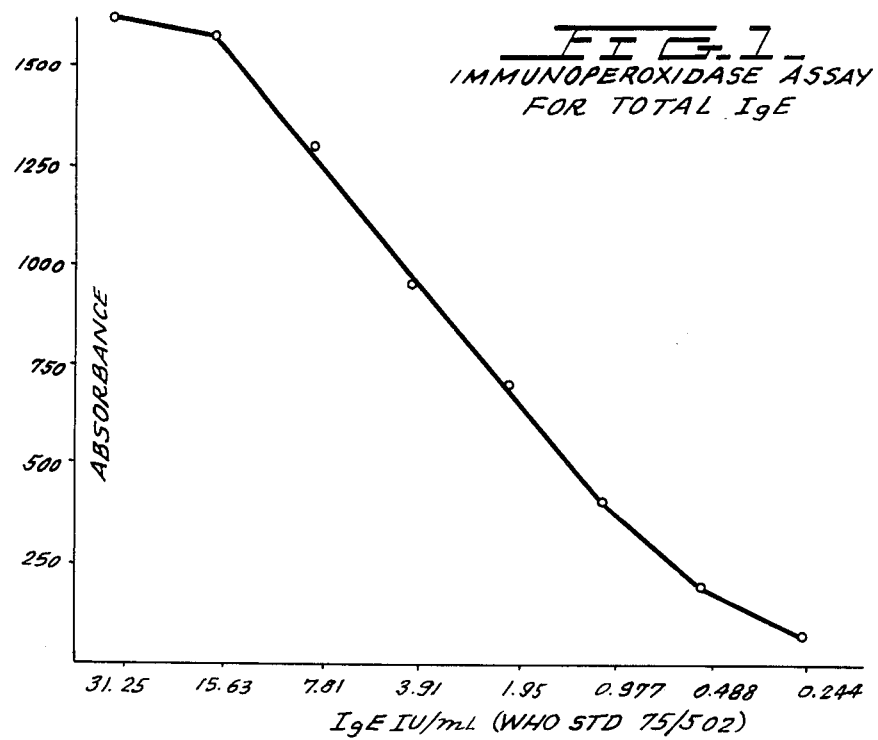

United States Patent [19]

Ali et al.

[11] Patent Number: 4,564,600

[45] Date of Patent: Jan. 14, 1986

[54] ALLERGENS AND ANTIBODIES FROM ALLERGEN EXTRACTS AND POOLED SERUM

[76] Inventors: Majid Ali, 19 Edgemont Pl., 07666; Madhava P. Ramanarayanan, 271 Briarcliffe Rd., both of Teaneck, N.J. 07666

[21] Appl. No.: 436,660

[22] Filed: Oct. 26, 1982

[51] Int. Cl.$^4$ ............................................. A61K 39/00
[52] U.S. Cl. ..................................... 436/513; 424/88; 424/91; 436/539; 436/547; 436/824
[58] Field of Search ............... 436/513, 539, 824, 547; 424/88, 91

[56] References Cited

U.S. PATENT DOCUMENTS

| | | | |
|---|---|---|---|
| 2,901,398 | 8/1959 | Perlman | 436/513 X |
| 3,953,588 | 4/1976 | Nieschulz | 424/91 X |
| 3,984,532 | 10/1976 | de Castro | 436/539 X |
| 3,995,023 | 11/1976 | Nieschulz | 424/91 X |
| 4,027,006 | 5/1977 | Nieschulz | 436/513 X |
| 4,031,199 | 6/1977 | Nieschulz | 436/513 X |
| 4,148,869 | 4/1979 | Deaton | 436/539 X |
| 4,226,853 | 10/1980 | Marsh | 424/88 X |
| 4,243,651 | 1/1981 | Nalebuff | 436/513 |
| 4,256,833 | 3/1981 | Ali | 436/513 X |
| 4,350,686 | 9/1982 | Relyveld | 424/91 X |

OTHER PUBLICATIONS

Chemical Abstracts I, 88:48843w (1978).
Chemical Abstracts II, 90:101863x (1979).

*Primary Examiner*—Sidney Marantz
*Attorney, Agent, or Firm*—Ostrolenk, Faber, Gerb & Soffen

[57] ABSTRACT

Allergenic factors are isolated from antigen extracts by preparing a column with pooled serum from patients with allergy to a given allergen system and passing over this column a pool of allergen extracts from different sources. Allergen specific immunoglobulin antibodies in purified form are obtained by forming an antigen-specific antibody complex from serum containing the antibodies and a material containing the antigen, recovering the complex and disassociating it, forming a second complex of the antigen with an excess of a second antibody so as to realize a combination of the second complex, free first specific antibody and free second specific antibody and then separating the second complex from the free first and second antibodies.

18 Claims, 4 Drawing Figures

IMMUNOPEROXIDASE ASSAY FOR TOTAL IgE

IMMUNOPEROXIDASE ASSAY FOR ALLERGEN-SPECIFIC IgE ANTIBODIES

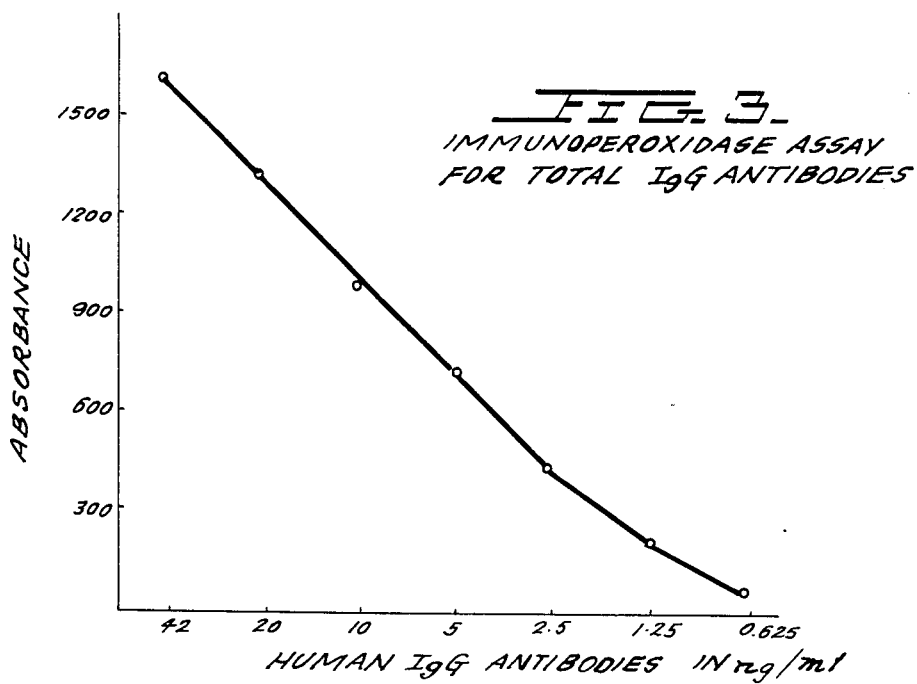
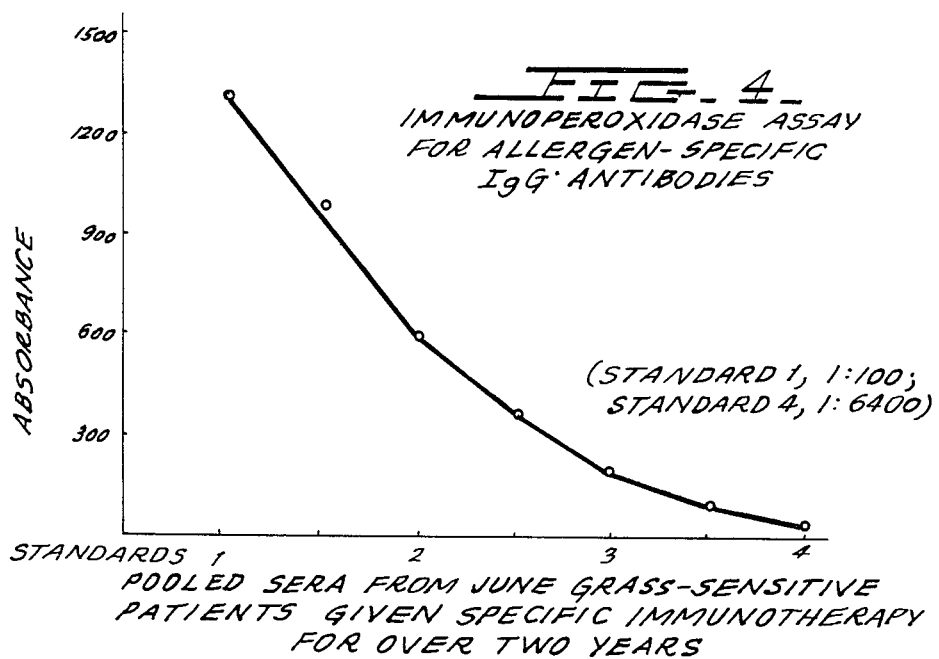

ALLERGENS AND ANTIBODIES FROM ALLERGEN EXTRACTS AND POOLED SERUM

BACKGROUND OF THE INVENTION

In 1921, Prausnitz and Küstner documented the presence of a transferable skin sensitizing factor in the serum of allergic patients and laid the cornerstone for the modern concepts of allergy. This serum factor was designated as reagin. The P-K transfer reaction became the essential investigative tool for the study of allergic disorders. In 1966, Ishizaka and colleagues linked the reaginic activity to antibodies belonging to the IgE class of immunoglobulins. Radioimmunoassay procedures were developed for the assay of serum level of total IgE antibodies and of allergen-specific IgE antibodies (the RAST test). It is clear that the RAST response for a given serum actually represents the sum of titers and avidities of the most of IgE antibodies with specificity for the various allergenic components of an allergen extract.

In the clinical practice of allergy, allergen extracts are used both in diagnosis and treatment. The extracts vary considerably in their potency as manifested by their ability to evoke a positive reaction in the human skin. Not unexpectedly, such variability in potency of different batches of extracts prepared by different manufacturers and even in different batches of extracts prepared by the same manufacturer has seriously hindered efforts to standardize allergy diagnosis, specific immunotherapy with injection with allergen extracts, and the in-vitro tests for monitoring the immunologic response to immunotherapy.

The variations in potency of extracts are largely caused by the diverse proteins and other allergenic components in any given allergen extract. The particular component, or more likely components, in any extract which cause the allergic response have not been satisfactorily identified. Fractionation of allergen extracts into their multiple allergenic factors by conventional techniques such as chemical, electrophoretic, isoelectric focusing, etc., would be extremely cumbersome and has not been attempted except on a limited scale.

At present, satisfactory potency standards are not available. Commercial extract preparations carry only an indirect indication of their content of allergenic components in terms of either weight/volume of allergen extract or protein nitrogen unit (PNU), the former being related to Noon units. Since the allergenic components of the extract represent only a small proportion of the extract, it is clear that these indirect indications can deviate from the actual quantity by a factor of several hundred to several thousands.

Several different approaches have been adopted to resolve these difficulties. The feasability of standardization of the potency of extracts by skin testing has been explored on a limited scale but there are several theoretical and practical barriers to this approach. A large number of suitable human volunteers would be required to do the necessary skin testing and there is a substantial risk of local and systemic (possibly fatal) reactions.

Another approach used in the past involves the measurement of the potency of the extract by its ability to inhibit the RAST reaction—the RAST inhibition test. This approach also faces several problems in that the RAST test itself has not been a standardized method. Attempts have been made to resolve this difficulty with the use of a "reference allergen extract" but this itself is a non-standardized preparation. Alternatively, serum containing known titers of allergen-specific IgE antibodies have been used for this purpose.

Figure 2:
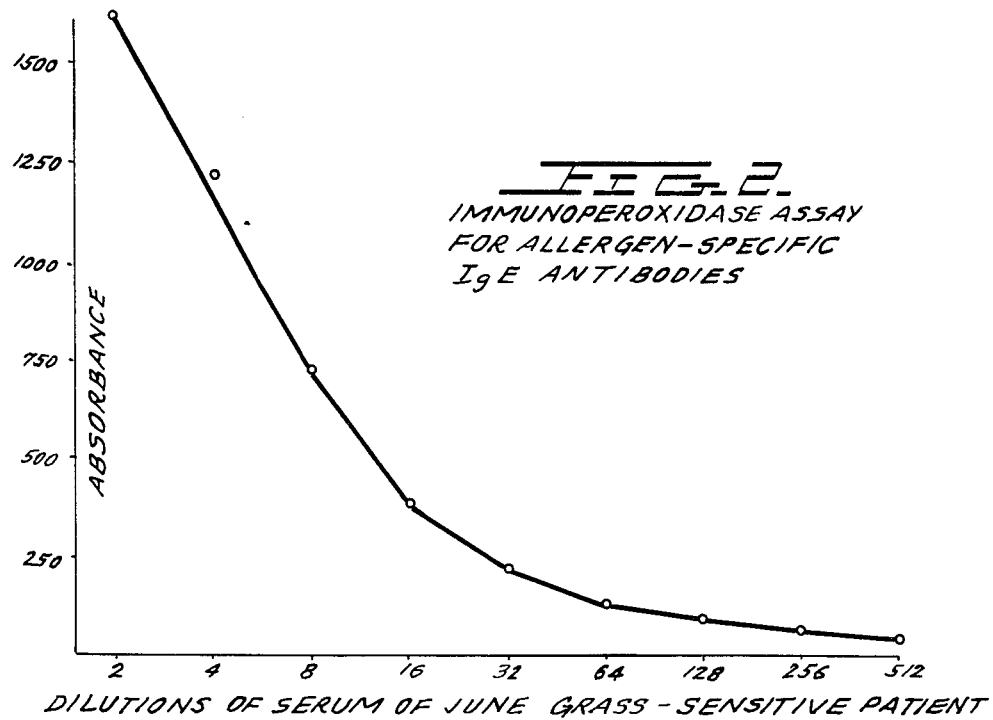

Since the assay for total IgE antibodies had been standardized with the use of WHO standard IgE material, efforts were made to standardize the RAST test by linking it to the radioimmunoassay procedure for total IgE and creating arbitrary units to express the concentration of allergen specific IgE, but this approach was unsatisfactory. This is because the basic test designs for the immunoassays for total and allergen-specific IgE antibodies are different; the immunosorbent for the total IgE assay is immobilized anti-IgE while that for specific IgE is immobilized allergen. Hence, the binding characteristics in the two systems are not expected to be comparable. FIGS. 1 and 2 illustrate this. Serum levels of allergen-specific IgE antibodies could not be quantitatively estimated as such material in purified form was not available for use as standards in constructing standard curves. Another approach adopted to standardize the results of the RAST test was based on the use of a time control and is designated the Modified RAST test. In this approach, the time required to obtain a given number of counts with a given number of units of WHO standard IgE run with a PRIST disc (anti-human IgE insolubilized on cyanogen bromide activated disc) and RAST isotope was measured and the time determined was used to count the bound radioactivity in the RAST test for all of the test samples. Thus, by varying the counting time, the absolute counts for the Modified RAST time control (and hence the modified RAST cut-off point) were kept constant. However, even this approach will provide only semi-quantitative estimation of the titer of the allergen specific IgE antibodies in the test serum because of a lack of suitable standards.

In addition to the above methods, attempts have been made to define the allergenic components in allergen extracts by gel diffusion precipitation techniques. This has been used on a limited scale for mite extract.

All of the above approaches share one common and serious handicap, namely the basic design of these methods does not include a purification step by which the small quantity of allergenic material (i.e., the multiple allergenic components) in an allergen extract can be separated from the bulk of the proteins and other substances which do not evoke an IgE response. In skin testing and RAST inhibition methods, a large number of substances are present which are of no clinical relevance because they do not induce an IgE response and can introduce error into the test results.

In 1935, it was recognized that specific immunotherapy for inhalent allergy induces the production of "blocking antibodies" which were subsequently found to belong to IgG class of immunoglobulins. Since then a large number of in-vivo and in-vitro methods have been developed to assess IgG response. Among these, the indirect methods include Prausnitz-Küstner neutralization, inhibition of in-vitro release of histamine from allergen-challenged leukocytes, hemagglutination of allergen-coated erythrocytes, and precipitation of IgG antibodies with staphylococcal protein A. The direct methods include radioimmunoassay and enzyme immunoassay. As for immunoassays for allergen-specific IgE antibodies, all the above methods for specific IgG antibodies yield only semi-quantitative results due to lack of standards containing purified material which can be quantified in nanograms or picograms.

The radioimmunoassays and enzyme immunoassay procedures which are being widely used today for the in vitro diagnosis of allergy and in-vivo monitoring of the immunologic responses to specific immunotherapy give only semiquantitative estimation of allergen specific IgE and IgG antibodies in the serum and direct quantitative measurement of these antibodies has not been possible to date. There has been no available technique for producing purified preparations of these antibodies for use as standards in a quantitative assay.

It is accordingly the object of this invention to provide techniques for isolating allergenic components from allergen extracts and for producing purified preparations of allergen specific IgE and IgG antibodies which can be used as standards in quantitative radioimmunoassays and enzyme immunoassays. This and other objects of the invention will become apparent to those skilled in the art from the following detailed description.

SUMMARY OF THE INVENTION

This invention relates to a method for isolation of allergenic factors from allergen extracts and for producing purified preparations of allergen specific IgE and IgG antibodies. The method involves the formation of an antigen-specific antibody complex from serum containing those antibodies and a material containing the antigen which is separated and disassociated followed by forming a second complex of the antigen with a second antibody which complex is separated to provide the free first allergen-specific IgE antibodies.

DESCRIPTION OF THE INVENTION

In accordance with the present invention, a method is provided for the isolation of allergenic components from allergen extracts and the preparation of allergen-specific IgE and IgG antibodies which can be used for preparing standard curves for use in in vitro tests and which permits the test results to be expressed in picograms (pg) or nanograms (ng). The method is based on the recognition and/or discovery of the following:

(1) there are several allergenic components in a given commercially available allergen extract;

(2) allergic individuals can manifest allergic reaction in response to one or more of these allergenic components;

(3) pooled serum from a sufficiently large number of patients with allergy to a given allergen will have an extremely high probability of including almost all of the antibodies to the allergenic components in a particular allergen extract;

(4) a pool of allergenic extracts for a given antigen system such as, e.g., June grass, from different commercial sources will have a very high probability of including all the allergenic components in that antigen system capable of evoking an allergenic response;

(5) when the pooled serum and pooled allergen extracts are incubated under suitable conditions, immune complexes will form between the allergenic components in the pooled allergen extract and the IgE and IgG antibodies with specificity for those allergenic components in the pooled serum;

(6) the immune complexes can be separated from the mixed pools under suitable conditions; and (7) it is possible to separate the allergen-specific IgE and IgG antibodies for dissociating the immune complexes under certain conditions.

The materials prepared by the process of the present invention are preparations of allergenic factors isolated from allergen extracts for use in allergy diagnosis and treatment, and purified preparations of IgE and IgG antibodies with specificity for various allergenic components quantified in nanograms or picograms and can now be used as a standard for quantitative assay of allergen-specific IgE and IgG antibodies in an enzyme immunoassay or radioimmunoassay system with the results expressed in absolute units, i.e., in picograms or nanograms. Similarly, the process of this invention can be used to prepare any immunoglobulin antibody, e.g., IgM, IgD and IgA with specificity for a given antigen in purified form.

Batches of antigen extracts are pooled together and are preferably dialyzed to remove extraneous material. We prefer to use extracts from various commercial sources since this increases the probability that all of the allergenic factors will be present. For example, 5 ml of June grass extracts from Antigen Laboratories, Pharmacia Diagnostics, Hollister-Stier Laboratories, Greer Laboratories and Center Laboratories were pooled and dialyzed with a cellulose dialyzer tubing obtained from Fisher Scientific.

Batches of serum from a plurality of allergenic patients who have been determined to have a high degree of sensitivity to, e.g., June grass, as determined by a diagnostic skin test and/or in vitro assay, are pooled. We have found that pooled serum of 5 to 10 individuals have been satisfactory but less or more individuals can be used as the source of the serum if desired. Human serum contains about 60,000,000 nanograms of protein per ml of which about 40,000,000 nanograms is albumin, 10,000,000 nanograms is IgG, and only about 275 nanograms if IgE. It is preferred to remove the albumin and other extraneous proteinaceous matter by the standard techniques of salting out with ammonium sulfate or sodium sulfate precipitation and subjecting the gamma-globulin fraction to dialysis. The resulting serum contains about 10,000,000 ng of IgG, about 1,000,000 ng each of IgA and IgM, about 400 ng IgD and about 275 ng of IgE.

For isolation of allergenic factors from allergen extracts, the pooled extracts and pooled sera are mixed under conditions which permit the antigen-antigen specific antibody immunocomplex to form. In general, for each 60 ml of serum, about 1 to 5 ml of extract (having a protein content of about 1 mg per ml) can be used and preferably about 2 ml of extract is employed. Conveniently, if desired, the antigen specific antibodies can be immobilized, for example, on cyanogen bromide activated agarose, in accordance with standard affinity chromatography techniques. The allergen extracts are passed through a column containing the immobilized antibodies and the allergenic components capable of evoking an IgE response bind to the antibodies adsorbed on the column from the pooled serum. The allergenic factors are then separated from the immobilizing solid and the allergenic factors are eluted by passing a suitable eluting liquid through the column.

As regards the method of the present invention for purification of specific IgE, the antigen-specific IgE complex is disassociated. The formation and dissociation of the complex is a function of pH and therefore the desired dissociation is accomplished by altering the pH to make it more acid. Conveniently, the standard glycine hydrochloric acid buffer which has a pH of 2.5 can be used and the mixture of the precipitate with this pH buffer will result in free antigen and specific IgE.

It is now necessary to separate the antigen from the antigen-specific IgE. Reestablishing a neutral pH will merely result in a reformation of the complex. To overcome this problem, a second antibody which will form immune complexes with the antigen is added. There are specific IgG antibodies which will form a complex with the antigens which form complexes with IgE. Since IgG and IgE compete for the antigen and it is desired to isolate the IgE, IgG is added in excess to increase the likelihood of IgG-antigen complex formation. The ratio of the added IgG to the IgE in the dissociated complex can be about 5:1 to 200:1 or more. We have found a ratio of about 10:1 to be convenient and while any amount of IgG above this amount as desired can be used we have not found any advantages in doing so. An estimate of the amount of specific IgE present by comparison with any known test for total IgE (FIGS. 1 and 2) is sufficient to determine the amount of IgG to be used. The pH of the system is then readjusted to a value at which the immune complexes can be formed by, for example, changing the buffer system to establish a pH of about 7.6. Because the IgG is present in such a large excess, substantially all of the complex which forms will be antigen-IgG. The complex is then precipitated by the addition of a suitable precipitating agent and the solid separated from the supernatant. As in the prior precipitation and separation step, this can be accomplished by the standard techniques of polyethylene glycol precipitation and centrifuging. The supernatant contains specific IgG, specific IgE and the polyethylene glycol precipitating agent. The precipitating agent can be removed by dialysis. While the resulting product contains free specific IgG which was not consumed in forming the immune complexes in a ratio, according to the preferred procedure, in the neighborhood of 10:1 to IgE, the presence of the IgG in the preparation is not significant in using the preparation as a standard since the ratio of IgG to IgE in serum is normally more than 3000 to 1. However, we chose to separate IgG by solid-phase immunoabsorption with affinity-purified anti-IgG.

The resulting purified IgE can be concentrated or diluted in order to prepare standard preparations containing any given amount of IgE antibodies with specificity for the particular antigen, e.g., containing 25, 100, 400 and 1600 pg of IgE antibodies. These standards can be used in direct quantitative immunoassays for the measurement of allergen specific IgE antibodies. Because the standards are true standards, the results of the enzyme immunoassay or radioimmunoassay systems can be stated in picograms or nanograms. Also because of the high purity of the allergen factors in the product, an immense number of diagnostic assays or immunotherapy doses can be prepared according to the invention from a small amount of pooled serum. For example, 60 ml of pooled serum from eight patients with high levels of sensitivity to June grass can be used to prepare highly immunopurified preparation of allergenic factors in June grass extract sufficient for performing 25,000 assays by an enzyme immunoassay or for 25,000 injections at the average dose equivalent to 0.1 ml of 1:500 w/v of a commercially available extract. Because of the high purity, analysis of the preparation for protein nitrogen content by commonly used chemical analysis now provides a true value. In one instance, the total quantity of specific IgE recovered from 60 ml of serum obtained by pooling 10 ml from each of 10 allergic patients with a high degree of sensitivity to June grass was 28,800 ng. We have found the quantity of specific IgE required for constructing a standard curve for a single assay run is about 2 ng, and therefore the number of assays possible with the product obtained from the 60 ml of pooled serum is about 14,000.

The following example for antigen specific IgE illustrates the invention.

All the glassware used in the procedure was siliconized and all the plastic ware used was made of polyethylene or polypropylene. The dialyzer tubing used was from Fisher Scientific Company, Springfield, N.J., and had a cutoff of 12,000 daltons, and was used after boiling in 5 millimolar EDTA, pH 8.0. All protein determinations were performed by the procedure of Lowry et al. (J. Biol. Chem. 193:1951, 265).

One ml of June grass allergenic extract from each of the five commercial sources were pooled and dialysed. The dialysed material (8.4 ml) contained a total of 7.73 mg protein (0.92 mg/ml). This is referred to as the pooled allergenic extract.

Six patients with a high degree of sensitivity to June grass allergens, as determined by diagnostic skin-test, a radioimmunoassay for June grass-specific IgE in the blood serum, as well as by an enzyme immunoassay for the determination of serum levels of June grass-specific IgE, and who had not previously received any immunotherapy treatment for allergy to June grass allergens were chosen. 10 ml of serum from each such patient was obtained and pooled. The pooled serum was clarified by centrifugation to remove any particulate material. Clarified serum measured 60 ml. An aliquot of the pool assayed by an enzyme immunoassay and by a radioimmunoassay gave an estimate of June grass allergen-specific IgE equivalent to 220 IU/ml. This estimation of the serum content of allergen-specific IgE was based on the calibration of the curve for the enzyme immunoassay for allergen-specific IgE with a total IgE curve built with WHO standard #75-502 material (FIGS. 1 and 2). Therefore, 60 ml of the pool is to contain an estimated allergen-specific IgE equivalent to 13,200 IU; since one IU of IgE is 2.5 nanograms (ng), this amounts to 33,000 ng or 33 ug of IgE, with specificity for June grass allergens.

To 60 ml of the pooled serum in a 400 ml pyrex beaker was added 5 ml of the pooled extract, and the mixture was stirred gently with a magnetic stirrer overnight (16 hours) at 4° C. so as to permit all the allergen-specific IgE in the serum to complex with the allergenic components in the allergenic extract, and thus form the allergen-IgE immune complex.

To the stirred mixture was added 130 ml of a 25% w/v solution of polyethylene glycol 6000 in phosphate buffered saline (PBS) and stirred again for 16 hours at 4° C. so as to precipitate and immune complexes formed. The mixture was centrifuged at 12,000×g for 15 minutes at 4° C. in corex tubes.

The supernatant was recovered by careful decantation, and saved for analysis. The pellet containing the immune complexes was resuspended in 200 ul of 0.1M glycine-HCl, pH 2.8, left standing at 4° C. for 2 hours and then centrifuged at 12,000×g for 15 minutes at 4° C. The supernatant (acid eluate) containing the solubilized immune complexes was recovered and saved. A small pellet containing some of the allergen-IgE complex yet to be solubilized was resuspended in 200 ml of saline with pH adjusted to 12 with ammonia and left standing at 4° C. for 2 hours. An almost clear solution was obtained. This was centrifuged at 12,000×g for 15 minutes at 4° C. The clear supernatant (base eluate) was carefully recovered and saved.

To the acid eluate was added 300 ug of affinity purified June grass allergen-specific IgG (approximately ten fold excess) in a volume of 750 ul. The resulting mixture was added to the base eluate, mixed by gentle vortexing, pH checked and adjusted to 7.7 by adding a few drops of 0.1M ammonia. This mixture was allowed to stand at 4° C. for 6 hours, with occasional agitation. Under these conditions, the allergen-IgG complex was allowed to form. Since affinity purified June grass allergen-specific IgG is employed in approximately a ten-fold excess, the ratio of the probability of the formation of the allergen-IgG complex to the formation of the allergen-IgE complex (because of the pH conditions) is expected to proceed at a ratio of 10 to 1 (assuming that the avidities of the IgG and IgE are equal; preliminary data indicates that the avidities of the IgG are higher than the IgE). As a result, the bulk of the allergen-specific IgE was now in free form.

To the mixture was then added 2.4 ml of 25% w/v solution of polyethylene glycol 6000 in PBS and the new mixture was left standing at 4° C. for 16 hours to permit optimal precipitation of the allergen-IgG complexes. The precipitated immune complexes were separated by centrifugation at 12,000×g for 15 minutes at 4° C.

The clear supernatant was carefully recovered and dialysed against 100 volumes of PBS, with four changes, at 4° C., to remove all the contaminating polyethylene glycol, over a period of 16 hours. The dialysate contained the allergen-specific IgE and some allergen-specific IgG, not removed through immune complex formation followed by precipitation.

The dialysate was stirred with 200 ul (packed volume) of affinity purified anti-human IgG bound to Sepharose 4B (an immunosorbant containing 2 mg of immobilized antibody in a 200 ul packed volume) over a period of 16 hours at 4° C. to remove any remaining IgG by solid-phase immunoabsorption.

The final supernatant containing only June grass allergen-specific IgE was considered a pure preparation of allergen-specific IgE. The IgE content of this preparation was assayed by an enzyme immunoassay and by a radioimmunoassay and the preparation (1.2 ml) was found to contain 1.3 IU (3.25 ng) of human IgE at a 1:800 dilution. This translates into 26,000 ng/ml of IgE, amounting to a total of 31,200 ng or 31.2 ug of allergen-specific human IgE.

Now that the June grass allergen-specific IgE has been obtained in a pure form, it can be suitably diluted in an appropriate buffer with additives and preservatives to ensure its stability both in terms of its nature as an IgE molecule and its immunoreactivity for, June grass allergens. This material can therefore be used to generate standard material in the assays for June grass specific IgE, wherein the allergen-specific IgE content can be now expressed in absolute amounts, such as nanograms or picograms, as the case may be, in relation to the standard material.

The allergen-specific IgG was obtained as follows. Ten ml of June grass allergenic extract from each of five commercial sources were pooled, dialysed in cellulose dialyzer tubing against 100 volumes of PBS, pH 7.7, overnight (16 hours) at 4° C., with three changes of the dialysis buffer. The dialysed extract volume was 82 ml and the protein content of the dialysed extract was found to be 0.92 mg/ml. The extract was immobilized on cyanogen bromide activated Sepharose 4B (2 grams of Sepharose, dry weight; 5 ml wet packed volume) and packed into an Econocolumn (1×10 cm) and equilibrated with PBS, pH 7.7.

Ten ml of serum from each of ten patients allergic to June grass and treated with immunotherapy using June grass allergenic extract for over two years, was obtained and pooled. An aliquot of the pool was assayed by enzyme immunoassays for both total and allergen-specific IgG antibodies and was estimated (by approximate calibration) to contain 6 micrograms (ug) of IgG per ml with specificity for June grass allergens (FIGS. 3 and 4). The serum pool was passed through the column with recycling at room temperature over a period of 12 hours. The column was then washed extensively with 100 ml PBS to remove all unbound serum proteins.

The column was eluted with 10 ml of 0.1M glycine-HCl, pH 2.8, followed by 15 ml of saline with the pH adjusted to 11 with ammonium hydroxide. Those fractions from both eluates containing protein were combined, and the pH adjusted to 7.7 by adding 0.1M ammonium hydroxide. The pooled, neutralized eluate was heated at 56° C. for one hour to remove by inactivation any allergen-specific IgE that may have been eluted along with the allergen-specific IgG. The heat-treated eluate is concentrated by precipitation with an equal volume of 36% w/v sodium sulfate. The precipitated material was collected by centrifugation at 12,000×g at 15° C., dissolved in PBS and dialysed against 100 volumes of PBS. The dialysate is clarified by centrifugation.

The clarified material (June grass allergen-specific IgG) was 1.3 ml and was found to contain 400 ug protein per ml, amounting to a total amount of 520 ug recovered.

The various embodiments which have been disclosed herein were for the purpose of further illustrating the invention but were not intended to limit it.

What is claimed is:

1. A method of isolating allergenic components from allergen extracts and of obtaining purified antigen-specific antibodies comprising forming an antigen-specific antibody complex from pooled serum containing said antibodies and pooled material containing said antigen, and separating said complex from said serum and material.

2. A method of isolating allergenic components from allergen extracts and of obtaining purified antigen-specific antibodies comprising
   forming a first antigen-specific antibody complex from serum containing said antibodies and a material containing said antigen, separating said first complex from said serum and material, dissociating said first complex, forming a second complex by mixing the dissociated first complex with an excess of a second antibody specific for said antigen so as to obtain a mixture of said second complex of antigen-second antibody, free first antibody and free second antibody, and separating said second complex from said free first and second antibodies.

3. The method of claim 2 so as to obtain purified specific IgE and IgG comprising
   (a) pooling serum of a plurality of allergic individuals,
   (b) pooling a plurality of allergen extracts, (c) mixing the said pooled serum and pooled extracts under conditions permitting the formation of a first antigen complex, (d) separating the first complex from the mixed pools, (e) dissociating the first complex, (f) mixing the dissociated first complex with excess antigen specific IgG or antigen specific IgE, (g) forming a second antigen immunoglobulin complex and (h) separating the second antigen complex from free specific immunoglobulin.

4. The method of claim 3 wherein the first antigen complex and second antigen complex separation steps comprise precipitation, and wherein the steps of dissociating the first antigen complex and forming the second antigen complex are effected by pH adjustment.

5. The method of claim 4 wherein the precipitation is effected by employing polyethylene glycol as a precipitating agent.

6. The method of claim 5 wherein the dissociation is effected by adjusting the pH to about 2.5 and the formation of the second antigen complex is effected by adjusting the pH to about 7.6.

7. The method of claim 6, wherein the ratio of added antigen specific IgG or IgE to IgE or IgG, respectively, of the dissociated first complex in step (f) is at least 5:1.

8. The method of claim 7 wherein the ratio is about 10:1.

9. The method of claim 8 wherein the pooled sera are dialyzed gamma-globulin fraction pooled sera and a quantity of pooled extract having a protein content about 1-5 mg is mixed with each 60 ml of pooled serum.

10. The method of claim 3 for obtaining purified specific IgE wherein the excess specific IgG or IgE in step (f) is antigen specific IgG.

11. The method of claim 3 for obtaining purified specific IgG wherein the excess specific IgG or IgE in step (f) is antigen specific IgE.

12. The product of the process of claim 2 comprising the free first and second antibodies which are specific IgG and specific IgE and in which said immunoglobulins are present in a ratio of less than about 200:1.

13. The product of claim 12 having a ratio of less than about 100:1.

14. The product of claim 13 in which the ratio is of IgE to IgG.

15. The product of claim 14 having a ratio of about 10:1.

16. The product of the process of claim 3 comprising free first and second immunoglobulins which are specific IgG and specific IgE and in which said IgG and IgE are present in a ratio of less than about 200:1.

17. The product of claim 16 in which the ratio is of IgE to IgG.

18. The product of claim 17 having a ratio of about 10:1.

* * * * *